US010769257B2

(12) United States Patent
Lee et al.

(10) Patent No.: US 10,769,257 B2
(45) Date of Patent: *Sep. 8, 2020

(54) VARIABLE BIOMETRIC INFORMATION-BASED COMPLEX AUTHENTICATION SYSTEM AND COMPLEX AUTHENTICATION METHOD USING THE SAME

(71) Applicants: Jin Hyuk Lee, Seoul (KR); FORC&C CO., LTD., Seoul (KR)

(72) Inventors: Jin Hyuk Lee, Seoul (KR); Yoon Hee Koo, Seoul (KR)

(73) Assignees: Jin Hyuk Lee, Seoul (KR); FORC&C CO., LTD., Seoul (KR)

( * ) Notice: Subject to any disclaimer, the term of this patent is extended or adjusted under 35 U.S.C. 154(b) by 241 days.

This patent is subject to a terminal disclaimer.

(21) Appl. No.: 15/763,725

(22) PCT Filed: Oct. 30, 2017

(86) PCT No.: PCT/KR2017/012049
§ 371 (c)(1),
(2) Date: Mar. 27, 2018

(87) PCT Pub. No.: WO2018/169160
PCT Pub. Date: Sep. 20, 2018

(65) Prior Publication Data
US 2019/0392126 A1 Dec. 26, 2019

(30) Foreign Application Priority Data
Mar. 17, 2017 (KR) ........................ 10-2017-0033838

(51) Int. Cl.
*G06F 21/32* (2013.01)
*G06F 21/45* (2013.01)
(Continued)

(52) U.S. Cl.
CPC .............. *G06F 21/32* (2013.01); *G06F 21/45* (2013.01); *H04L 9/32* (2013.01);
(Continued)

(58) Field of Classification Search
CPC .. G06F 21/32; G06F 21/45; G06F 2221/2141; H04L 9/32; H04W 12/00;
(Continued)

(56) References Cited

U.S. PATENT DOCUMENTS 5,229,764 A * 7/1993 Matchett ........... H04W 12/1206
340/5.52
7,167,987 B2 * 1/2007 Angelo ................... G06F 21/32
713/186
(Continued)

FOREIGN PATENT DOCUMENTS

JP 2007-213196 A 8/2007
JP 2007-265219 A 10/2007
(Continued)

OTHER PUBLICATIONS

International Search Report in International Application No. PCT/KR2017/012046, filed Oct. 30, 2017.
International Search Report in International Application No. PCT/KR2017/012049, filed Oct. 30, 2017.
Supplementary European Search Report dated May 6, 2020 in European Application No. 17859366.1.

*Primary Examiner* — Jayesh M Jhaveri
(74) *Attorney, Agent, or Firm* — Saliwanchik, Lloyd & Eisenschenk

(57) ABSTRACT

A complex authentication system that uses personal variable biometric information which changes according to times and environments, and a complex authentication method using the same are disclosed. The variable biometric information-based complex authentication system includes: a mobile terminal configured to collect variable biometric information; a variable biometric information management server configured to store the variable biometric information
(Continued)

received from the mobile terminal; and an agent server configured to, when the mobile terminal requests a login command regarding the ID, verify validity of the login command regarding the ID based on the variable biometric information. Accordingly, even if biometric information used in an authentication procedure is leaked, a damage resulting therefrom can be inhibited, and security of the authentication procedure can be enhanced by combining different types of variable biometric information or by combining variable biometric information of a plurality of users.

9 Claims, 10 Drawing Sheets

(51) Int. Cl.
    *H04L 9/32*         (2006.01)
    *H04W 12/00*      (2009.01)
    *H04W 12/06*      (2009.01)

(52) U.S. Cl.
    CPC ... *G06F 2221/2141* (2013.01); *H04W 12/002* (2019.01); *H04W 12/0608* (2019.01)

(58) Field of Classification Search
    CPC .............. H04W 12/06; H04W 12/002; H04W 12/0608
    See application file for complete search history.

(56) References Cited

U.S. PATENT DOCUMENTS

| | | | |
|---|---|---|---|
| 2005/0273339 A1* | 12/2005 | Chaudhari | G10L 15/26 704/270 |
| 2009/0106558 A1* | 4/2009 | Delgrosso | G06F 21/41 713/184 |
| 2013/0227651 A1* | 8/2013 | Schultz | G06F 21/32 726/4 |
| 2014/0188770 A1 | 7/2014 | Agrafioti et al. | |
| 2015/0347734 A1* | 12/2015 | Beigi | G06F 21/32 713/155 |
| 2016/0142405 A1* | 5/2016 | Deffeyes | H04L 63/0861 726/7 |
| 2016/0283703 A1* | 9/2016 | Allyn | G06F 21/32 |

FOREIGN PATENT DOCUMENTS

| | | |
|---|---|---|
| JP | 2008-064928 A | 3/2008 |
| JP | 2012-212362 A | 11/2012 |
| KR | 10-2002-0081121 A | 10/2002 |
| KR | 10-2006-0063664 A | 6/2006 |
| KR | 10-1575763 B1 | 12/2015 |
| KR | 10-1756059 B1 | 7/2017 |
| WO | WO-2015/039084 A1 | 3/2015 |

\* cited by examiner

VARIABLE BIOMETRIC INFORMATION-BASED COMPLEX AUTHENTICATION SYSTEM AND COMPLEX AUTHENTICATION METHOD USING THE SAME

CROSS-REFERENCE TO RELATED APPLICATIONS

This application is the U.S. national stage application of International Patent Application No. PCT/KR2017/012049, filed Oct. 30, 2017, which claims priority to Korean Application No. 10-2017-0033838, filed Mar. 17, 2017, the disclosures of each of which are incorporated herein by reference in their entirety.

TECHNICAL FIELD

The present disclosure relates to a variable biometric information-based complex authentication system and a complex authentication method using the same, and more particularly, to a complex authentication system that uses personal variable biometric information which changes according to times and environments, and a complex authentication method using the same.

BACKGROUND ART

In general, a user of a computer needs to perform an authentication procedure to have an access authority by inputting his/her ID and password into a host computer or a network, in order to access limited information or to use a membership service.

Such an authentication procedure is increasingly used in various fields with the development of electronic commerce and the expansion of online financial service, and there is an increasing demand for a simpler and safer authentication procedure.

Specifically, FinTech services are expanding since methods for solving the inconvenience of having to go through a payment authentication procedure every time payment is made, such as PayPal™, have appeared, and various payments methods and complex authentication methods are appearing.

In recent years, not only mobile unlocking or password setting through fingerprint recognition or biometric information authentication through fingerprint recognition, but also various personal authentication, and personal identification systems and methods based on iris recognition, which has a higher identification accuracy than that of fingerprint recognition, are appearing.

However, such biometric information complex authentication systems and methods have limits since biometric information used therein is unique to each individual person, but is permanent, and thus has the risk of being leaked and illegally used.

In particular, in recent years, various services of FinTech are expanding, and various attempts to use personal biometric information in existing complex authentication methods such as mobile transfer, mobile payment, etc. are being made, and accordingly, methods for personal authentication and personal identification using personal biometric information are being applied. Therefore, such limits may become a big problem.

Amounts of produced data abruptly increase under the influence of social media, big data, IoT, etc., and cloud services which are popularly used are utilized for companies as well as for individuals, and web storage service are also increasingly used since a plurality of users can share specific data and use. However, since such cloud services or web storage services perform only personal authentication procedures simply by using users' passwords as authentication procedures to obtain an access authority, there is a problem that security is vulnerable.

Accordingly, in authentication procedures for cloud services or web storage service, there is a demand for a method for enhancing security through a complex authentication procedure, such as an solidarity authentication among a plurality of users of a set user group, rather than an authentication procedure using a personal password or biometric information, and also, there is a demand for a new concept complex authentication system and a complex authentication method, which can minimize a damage even if biometric information is leaked.

DISCLOSURE

Technical Problem

The present disclosure has been developed in order to address the above-discussed deficiencies of the prior art, and an object of the present disclosure is to provide a variable biometric information-based complex authentication system, which can selectively determine a security level of an authentication procedure, and performs the authentication procedure using personal variable biometric information, which changes according to times and environments, so as to inhibit a damage if the biometric information used in the authentication procedure is leaked, and a complex authentication method using the same.

In addition, another object of the present disclosure is to provide a variable biometric information-based complex authentication system which performs an authentication procedure by combining variable biometric information collected from a plurality of users, and sets different security levels to respective IDs of the plurality of users so as to enhance security through the complex authentication procedure among the plurality of users, and performs a solidarity authentication procedure to assess a facility or information requiring an access authority, and a complex authentication method using the same.

Technical Solution

According to an embodiment of the present disclosure to achieve the above-described object, a variable biometric information-based complex authentication system includes: a plurality of mobile terminals configured to generate information regarding an ID that intends to access a facility or information requiring an access authority, and to collect variable biometric information, such that the information regarding the ID and the variable biometric information are stored all together; a variable biometric information management server configured to receive the information regarding the ID and the variable biometric information from the plurality of mobile terminals, and to store the information; and an agent server configured to, when the mobile terminal requests a login command regarding the ID, compare variable biometric information received from the variable biometric information management server and variable biometric information received from the mobile terminal, and to verify validity of the login command regarding the ID.

In addition, the agent server may be configured to, when information regarding a specific ID is received from one of the plurality of mobile terminals, set the specific ID to an ID of a first security level which is able to independently access the facility or information requiring the access authority, or an ID of a second security level which is able to access the facility or information requiring the access authority dependently according to a login state of the ID of the first security level even when validity of the login command regarding the ID is verified.

In addition, the agent server may be configured to provide one or more IDs of the second security level that are set to be able to access the facility or information requiring the access authority only in a state where the ID of the first security level is logged in.

In addition, the agent server may be configured to, when a login command regarding the ID is requested, determine whether the ID requesting the login command is the ID of the first security level or the ID of the second security level, and the agent server may be configured to, when the ID requesting the login command is the ID of the first security level, verify only validity of the login command regarding the ID of the first security level, and, when the ID requesting the login command is the ID of the second security level, verify validity of the login command regarding the ID of the second security level only in the state where the ID of the first security level, which is set to authenticate in solidarity with the ID of the second security level, is logged in.

In addition, the agent server may be configured to variably change whether the ID intending to access the facility or information requiring the access authority is the ID of the first security level or the ID of the second security level with respect to the facility or information requiring the access authority according to settings.

In addition, the agent server may be configured to, when there are a plurality of facilities or a plurality of pieces of information requiring the access authority, individually set the ID, intending to access the facility or information requiring the access authority, to the ID of the first security level or the ID of the second security level with respect to the respective facilities or the respective piece of information requiring the access authority.

In addition, the plurality of terminals may be configured to collect the variable biometric information and to avoid transmitting a real value of the collected variable biometric information to the variable biometric information management server, and is configured to transmit only information regarding a figure or a form of a graph indicating a variation in a specific section.

In addition, the agent server may be configured to, when a login command regarding the specific ID is requested, compare a figure or a form of a graph included in variable biometric information received from the mobile terminal, and a figure or a form of a graph included in variable biometric information received from the variable biometric information management server on a real time basis, and to verify validity of the login command.

In addition, the variable biometric information management server may be configured to accumulate and store the variable biometric information including only information regarding the figure or the form of the graph according to the information regarding the ID, and, when the mobile terminal requests to discard variable biometric information stored for the specific ID, to discard the variable biometric information stored for the specific ID, and to accumulate and store variable biometric information, transmitted along with the information regarding the specific ID after the stored variable biometric information is discarded, according to the information regarding the ID.

The mobile terminal may be configured to, when two or more types of variable biometric information are collected, match respective pieces of classification information to the collected pieces of variable biometric information along with the information regarding the ID, such that the respective types of variable biometric information are identified.

In addition, the agent server may be configured to, when the two or more types of variable biometric information are collected, individually determine equivalence between first variable biometric information and second variable biometric information to which different classification is matched, and to verify validity of login commands regarding respective IDs generated by the plurality of mobile terminals.

In addition, the variable biometric information may include one or more pieces of information from among user's weight, body fat percentage, blood pressure, temperature, breathing rate, heart rate, blood glucose, muscle mass, total body water, protein, abdominal visceral fat, skeletal muscle mass, basal metabolic rate, exercise, number of steps, sleeping pattern, weight load pattern of both feet, and paces.

According to an embodiment of the present disclosure to achieve the above-described object, a variable biometric information-based complex authentication method includes the steps of: generating, by a mobile terminal, information regarding an ID that intends to access a facility or information requiring an access authority, and collecting variable biometric information and storing the variable biometric information along with the information regarding the ID; receiving the information regarding the ID and the variable biometric information from the mobile terminal, and storing the information in a variable biometric information management server; and, when the mobile terminal requests a login command regarding the ID, comparing, by an agent server, variable biometric information received from the variable biometric information management server and variable biometric information received from the mobile terminal, and verifying validity of the login command regarding the ID.

Advantageous Effects

1251 Accordingly, even if biometric information used in an authentication procedure is leaked, a damage resulting therefrom can be inhibited, and security of the authentication procedure can be enhanced by combining different types of variable biometric information or by combining variable biometric information of a plurality of users.

In addition, the authentication procedure is performed by combining variable biometric information collected from the plurality of users, and in particular, a solidarity authentication procedure to access a facility or information requiring an access authority may be performed by setting different security levels to respective IDs of the plurality of users.

In addition, as the security level of the authentication procedure is selectively determined, the system and the method of the present disclosure can be utilized as an authentication procedure to obtain an access authority regarding information stored in a network server, an authentication procedure for entering or exiting a facility such as an office or school, or an authentication procedure for financial services such as account transfer, payment, etc.

BEST MODE

Hereinafter, the present disclosure will be described in more detail with reference to the accompanying drawings. Exemplary embodiments introduced hereinafter are provided such that the idea of the present disclosure is fully conveyed to a person skilled in the art. The present disclosure is not limited to embodiments described below and may be specified in other forms.

Figure 1:
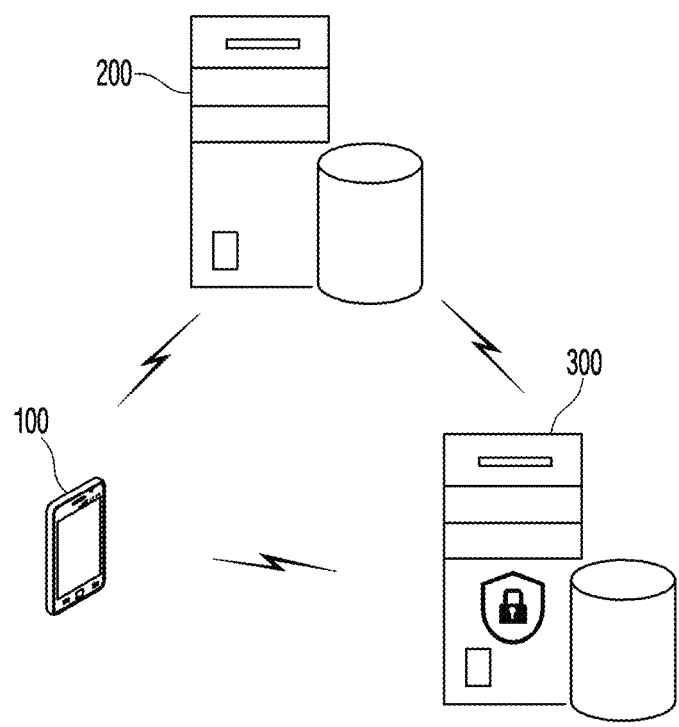
FIG. 1 is a view schematically showing a variable biometric information-based complex authentication system according to an embodiment of the present disclosure.
Figure 2:
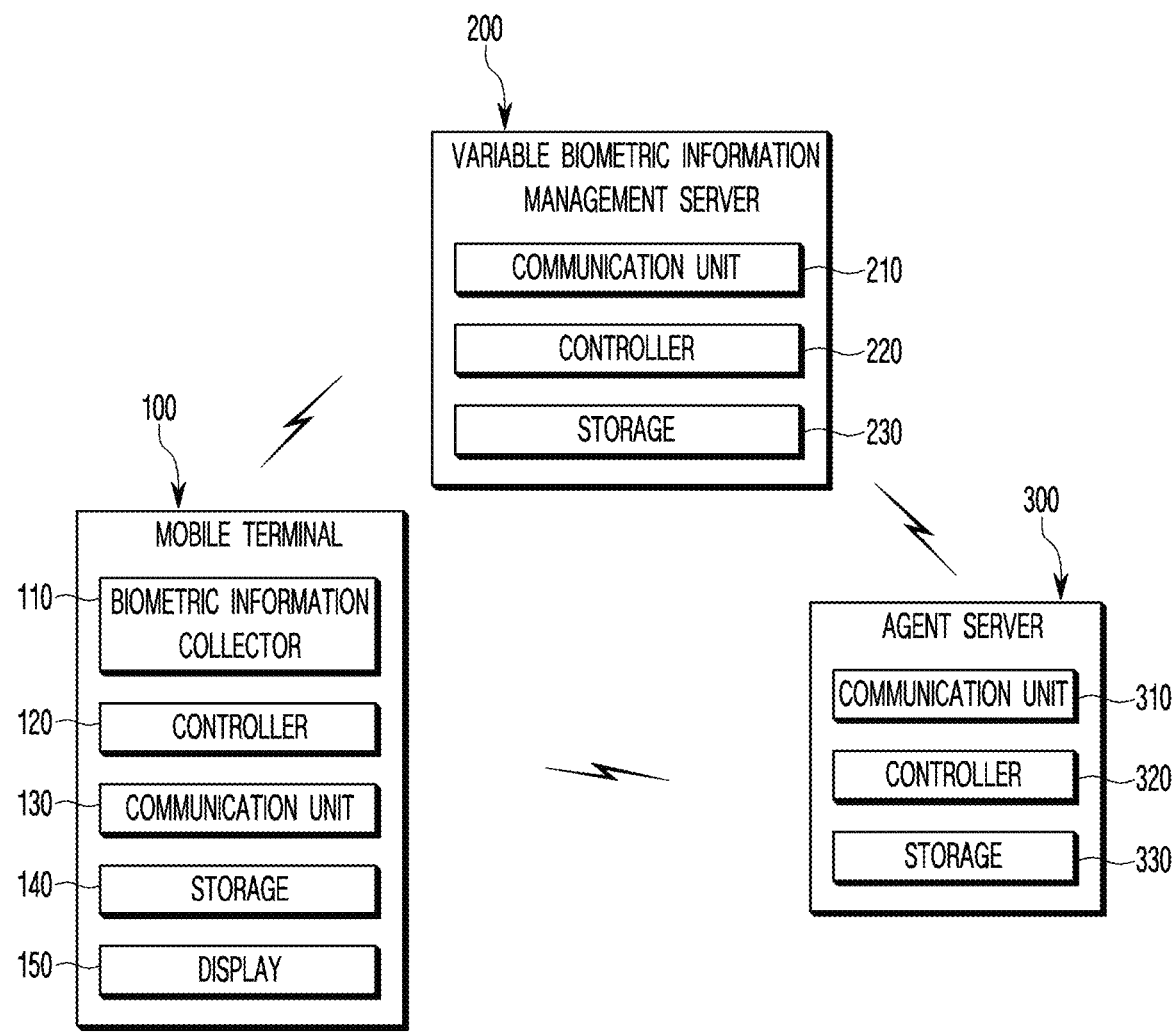
FIG. 2 is a block diagram provided to illustrate a configuration of a variable biometric information-based complex authentication system according to an embodiment of the present disclosure.

FIG. 1 is a view schematically showing a variable biometric information-based complex authentication system according to an embodiment of the present disclosure, and FIG. 2 is a block diagram provided to illustrate a configuration of a variable biometric information-based complex authentication system according to an embodiment of the present disclosure.

Figure 3:
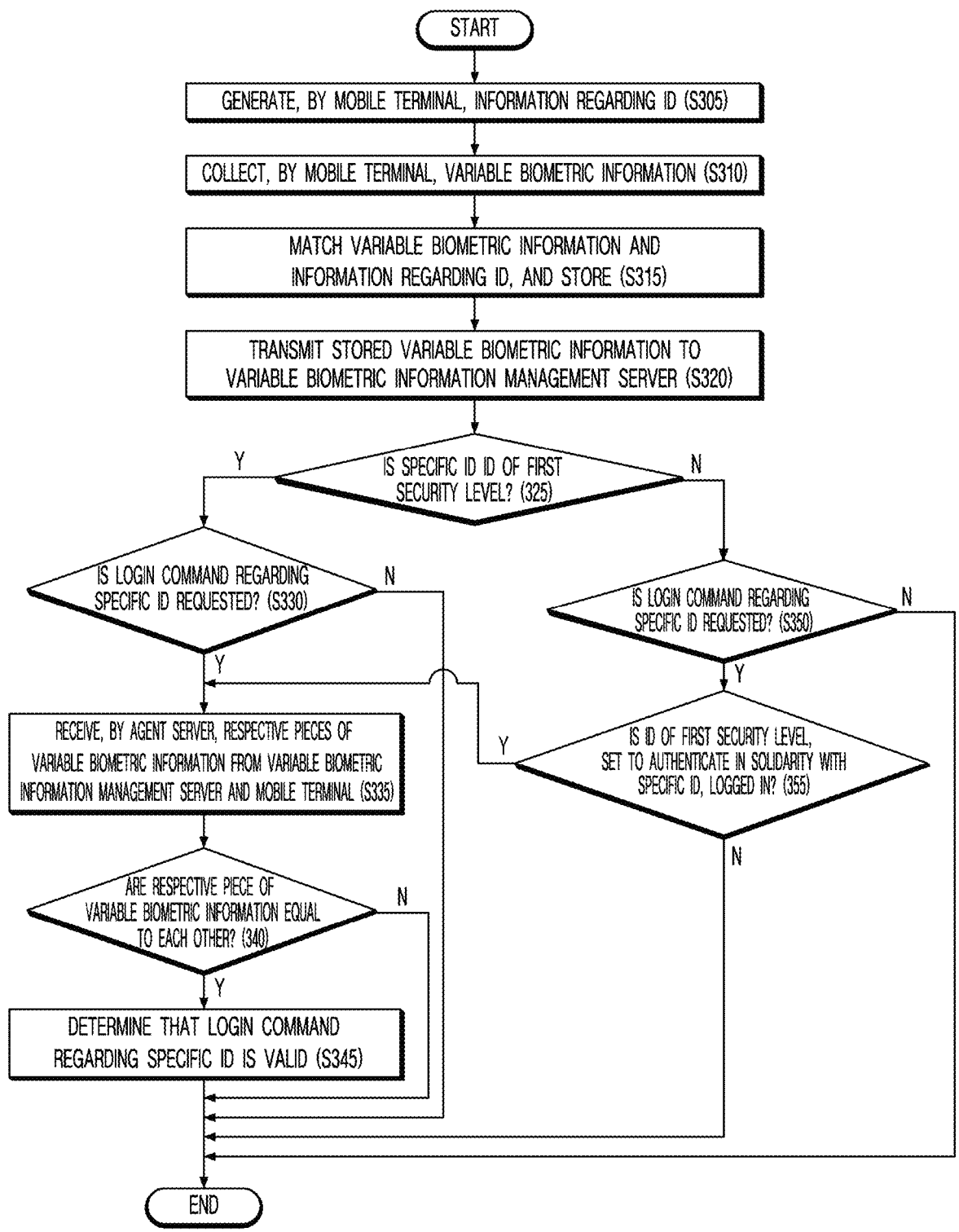
FIG. 3 is a view provided to illustrate a process of determining whether to access a facility or information requiring an access authority according to a security level of a specific ID in a variable biometric information-based complex authentication method according to an embodiment of the present disclosure.
Figure 4:
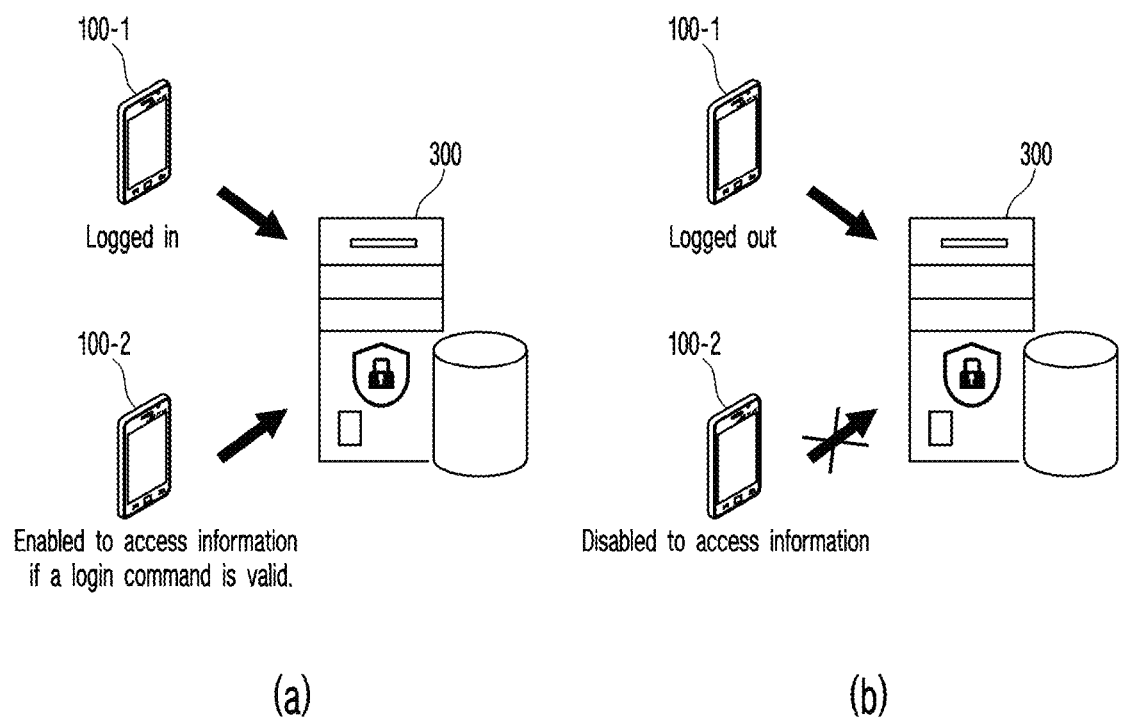
FIG. 4 is a view provided to illustrate a process of variably changing a security level of a specific ID according to a facility or information requiring an access authority in a variable biometric information-based complex authentication method according to an embodiment of the present disclosure.

In addition, FIG. 3 is a view provided to illustrate a process of determining whether to access a facility or information requiring an access authority according to a security level of a specific ID in a variable biometric information-based complex authentication method according to an embodiment of the present disclosure, and FIG. 4 is a view provided to illustrate a process of variably changing a security level of a specific ID according to a facility or information requiring an access authority in a variable biometric information-based complex authentication method according to an embodiment of the present disclosure.

Hereinafter, a variable biometric information-based complex authentication system (hereinafter, referred to as a "complex authentication system") according to an embodiment will be described with reference to FIGS. 1 to 4.

The complex authentication system according to an embodiment is provided to perform an authentication procedure using personal variable biometric information, which changes according to times and environments, so as to inhibit a damage even if the biometric information used in the authentication procedure is leaked, and also, is provided to perform the authentication procedure by combining different types of variable biometric information or by combining variable biometric information collected from a plurality of users.

To achieve this, the complex authentication system may include a mobile terminal 100, a variable biometric information management server 200, and an agent server 300.

Specifically, the mobile terminal 100 may be provided to generate information regarding an ID that intends to access a facility or information requiring an access authority, and to collect variable biometric information and to store the information regarding the ID and the variable biometric information all together.

Specifically, for example, the mobile terminal 100 may be implemented by using a device such as a smart phone or a smart watch, and may collect biometric information, such as user's weight, body fat percentage, blood pressure, temperature, breathing rate, heart rate, blood glucose, muscle mass, total body water, protein, abdominal visceral fat, skeletal muscle mass, basal metabolic rate, exercise, number of steps, sleeping pattern, weight load pattern of both feet, and paces, and may store the collected biometric information along with the information regarding the ID, or may transmit the collected variable biometric information to the variable biometric information management server 200 along with the information regarding the ID.

To achieve this, the mobile terminal 100 includes a biometric information collector 110, a controller 120, a communication unit 130, a storage 140, and a display 150.

The biometric information collector 110 of the mobile terminal is provided to collect variable biometric information.

Specifically, the biometric information collector 110 may be provided inside the mobile terminal 100 or may be provided outside the mobile terminal, like a smart scale, a smart blood pressure gauge, a smart blood glucose monitor, a smart watch, a smart band, and a smart shoe insole, to interwork with the mobile terminal 100, and may collect variable biometric information such as user's weight, body fat percentage, blood pressure, temperature, breathing rate, heart rate, blood glucose, muscle mass, total body water, protein, abdominal visceral fat, skeletal muscle mass, basal metabolic rate, exercise, number of steps, sleeping pattern, weight load pattern of both feet, and paces.

In this case, the mobile terminal 100 may be provided with a plurality of biometric information collectors 110 to collect various types of biometric information.

The controller 120 of the mobile terminal is provided to control elements of the mobile terminal 100 and to perform overall tasks of the mobile terminal 100.

Specifically, the controller 120 may generate information regarding an ID that intends to access a facility or information requiring an access authority, and may store variable biometric information collected by the biometric information collector 110 in the storage 140 along with the information regarding the ID, or may transmit the variable biometric information to the variable biometric information management server 200 or the agent server 300 along with the information regarding the ID via the communication unit 130.

The variable biometric information includes sensitive information related to user's personal information, diseases or health state, and thus, when such information is leaked, there may be concern about a damage caused by an illegal use of a password, and also, a more serious damage may be caused by personal information leakage.

Accordingly, the controller 120 may collect variable biometric information, but may not transmit a real value of the collected variable biometric information to the variable biometric information management server 200. Instead, the controller 12Q may transmit only information regarding a figure or a form of a graph indicating a variation in a specific section along with the information regarding the ID. Therefore, even when the variable biometric information transmitted to the variable biometric information management server 200 is leaked, a damage resulting therefrom can be minimized or inhibited.

In addition, in the case of the agent server 300, the controller 120 may transmit the real value of the collected variable biometric information to the agent server 300, such that the agent server 300 can extract the information regarding the figure or form of the graph indicating the variation in the specific section by itself. Therefore, when data including the real value of the variable biometric information stored in the storage 140 is deformed or damaged, a damage resulting therefrom can be minimized or inhibited.

In another example, the controller 120 may store the collected variable biometric information in the unit of a predetermined time, and may add time information regarding a collection time to the variable biometric information and store the information.

By doing so, the controller 120 may identify the collected plurality of pieces of variable biometric information according to collection times. Afterward, in the process of comparing, by the agent server 300, variable biometric information stored in the variable biometric information management server 200 and variable biometric information stored in the mobile terminal 100 to verify validity of a login command, the agent server 300 may compare only pieces of variable biometric information added with the same time information each other, such that time required to verify can be reduced and verification reliability can be enhanced.

That is, when a login command regarding an ID is requested, the agent server 300 may compare information regarding time, added to variable biometric information received from the mobile terminal 100, and stored information regarding time, and may determine equivalence therebetween, and, when it is determined that two pieces of time information are equal to each other, the agent server 300 may verify validity of the login command regarding the ID by determining whether stored variable biometric information and variable biometric information received after the login command is requested are equal to each other.

In addition, the controller 120 may generate information regarding an ID that intends to access a facility or information requiring an access authority, and may access the variable biometric information management server 200 and register an ID that can identify whose biometric information the variable biometric information is.

Specifically, for example, the controller 120 may register a plurality of IDs at the variable biometric information management server 200, and, even when the plurality of IDs are registered at the variable biometric information management information 200, the controller 120 may designate one ID, and may match information regarding the designated ID and variable biometric information and transmit the matched information.

In addition, when the mobile terminal 100 is connected to a short range communication network, the controller 120 may control to transmit the variable biometric information stored in the storage 140 to the variable biometric information management server 200 at predetermined time intervals.

By doing so, stored existing variable biometric information may be replaced with newly collected variable biometric information and may be updated, and, even when biometric information used in the authentication procedure is leaked, a damage resulting therefrom can be inhibited.

The communication unit 130 of the mobile terminal is provided to access the variable biometric information management server 200, the agent server 300, and other external servers using the communication network to perform Internet communication.

Specifically, the communication unit 130 may request a login command regarding a specific ID to the agent server 300, or may transmit collected variable biometric information to the variable biometric information management server 200 or the agent server 300.

The storage 140 of the mobile terminal is provided to store applications and data necessary for performing the tasks of the mobile terminal 100.

Specifically, the storage 140 may store information regarding an ID and variable biometric information all together.

In addition, the storage 140 may add time information regarding a collection time to the variable biometric information, and may store the information. In this case, the variable biometric information may be stored in the unit of a predetermined time.

Herein, the information regarding the time is information regarding a time at which variable biometric information is collected, and, when variable biometric information is expressed by a graph indicating a variation of a real value according to time, the variable biometric information may be expressed by graphs of various forms according to a time unit, and thus the information regarding the time may be an important factor in comparing variable biometric information.

The display 150 of the mobile terminal is provided to output information that the mobile terminal 100 intends to output.

In addition, the mobile terminal 100 may be provided with an input unit (not shown) to input a command related to a task to perform, and a battery unit (not shown) to supply power, in addition to the controller 120, the communication unit 130, the storage 140, and the display 150 described above.

The variable biometric information management server 200 is provided to manage variable biometric information received from the mobile terminal 100.

Specifically, when collected variable biometric information is received along with information regarding an ID, the variable biometric information management server 200 may store the received variable biometric information along with the information regarding the ID, and, when the agent server 300 requests variable biometric information stored along with information regarding a specific ID to verify validity of a login command regarding the specific ID, the variable biometric information management server 200 may transmit the stored variable biometric information to the agent server.

To achieve this, the variable biometric information management server 200 includes a communication unit 210, a controller 220, and a storage 230.

The communication unit 210 of the variable biometric information management server is provided to be connected with the mobile terminal 100 and the agent server 300 using a communication network and to perform Internet communication.

Specifically, the communication unit 210 may receive variable biometric information from the mobile terminal 100 or transmit stored biometric information to the agent server 300 according to a request of the agent server 300.

The controller 220 of the variable biometric information management server is provided to control elements of the variable biometric information management server 200 and to perform overall tasks of the variable biometric information management server 200.

Specifically, the controller 220 may control to store information regarding an ID and variable biometric information which are received from the mobile terminal 100 all together, and, when a login command regarding a specific ID is requested, the controller 220 may identify variable biometric information stored along with the information regarding the specific ID from the agent server 300, and may transmit the identified variable biometric information to the agent server 300.

Herein, the variable biometric information received from the mobile terminal 100 and the variable biometric information transmitted to the agent server 300 do not include a real value of the variable biometric information, and may include only information regarding a figure or a form of a graph indicating a variation in a specific section.

In this case, the ID may identify whose biometric information the variable biometric information is, and also, may be used to connect to a network such as a specific Internet page through the agent server 300 with a user making himself/herself known by the ID, or may be used to perform a task requiring an authority such as payment.

The storage 230 of the variable biometric information management server is provided to store programs and data necessary for performing tasks of the variable biometric information management server 200.

Specifically, the storage 230 may store the information regarding the ID and the variable biometric information, which are received from the mobile terminal 100 all together.

When the mobile terminal 100 requests a login command to access a host computer or a network with a specific ID, the agent server 300 may verify validity of the requested login command, and, when it is determined that the login command is valid, the agent server 300 may enable the mobile terminal 100 to access the host computer or network.

In addition, when the validity of the requested login command is verified, the agent server 300 may perform a task requiring an authority, such as payment, and, when an authentication procedure is required like an electronic payment command as well as the login command, the validity of the corresponding command may be verified in the same method, and the authentication procedure may be performed.

In this case, the agent server 300 may be provided with a separate server to directly perform the corresponding command, or, when the variable biometric information management server 200 performs the corresponding command, the agent server 300 may transmit information indicating whether the corresponding command is valid to the separate server performing the corresponding command or the variable biometric information management server 200, such that the corresponding command is performed.

In addition, when a plurality of agent servers 300 are provided, the respective mobile terminals 100 using different IDs may perform the authentication procedure through the respective agent servers 300.

In addition, the agent server 300 may perform a solidarity authentication procedure with respect to a plurality of IDs through the plurality of mobile terminals 100, rather than with respect to one ID, in order to provide an access authority regarding specific information.

Specifically, when a first mobile terminal 100-1 using a first ID requests a login command to obtain an access authority regarding specific information, the agent server 300 may receive respective pieces of variable biometric information from the first mobile terminal 100-1 and the variable biometric information management server 200, and compare the respective pieces of variable biometric information, thereby verifying validity of the login command regarding the first ID. Additionally, the agent server 300 may receive respective pieces of variable biometric information from a second mobile terminal 100-2 using a second ID, which is set to be authenticated in solidarity with the first ID, and from the variable biometric information management server 200, and compare the respective pieces of variable biometric information. In this case, only when the login command regarding the first ID and the login command regarding the second ID, which is set to be authenticated in solidarity with the first ID, are all determined to be valid, the agent server 300 may provide the access authority regarding the specific information to the first mobile terminal 100-1.

For example, in the case where variable biometric information used in the authentication procedure is a body fat percentage, when the first mobile terminal 100-1 through which a user A requests a login command using the first ID requests a login command for the authentication procedure to perform a payment task for e-commerce, the agent server 300 may receive information regarding the body fat percentage from the first mobile terminal 100-1 and the variable biometric information management server 200, and may verify validity of the login command regarding the first ID. Additionally, the agent server 300 may receive information regarding the body fat percentage from the second mobile terminal 100-2, through which a user B who is the user A's spouse tries to verify validity of a login command using the second ID, which is set to be authenticated in solidarity with the first ID, and, when the information regarding the body fat percentage of the user A and the information regarding the body fat percentage of the user B are all equal to the respective pieces of information regarding the body fat percentage received from the variable biometric information management server 200, the agent server 300 may determine that the login command is valid, and may perform the payment task.

In addition, such a solidarity authentication procedure may be set for a specific solidarity group such as a family, a couple, and a club, and may be utilized for a facility or information requiring an authentication procedure for an access authority, and for an authentication procedure for using a financial service such as electronic payment.

In addition, the agent server 300 may set different security levels for the plurality of IDs. In this case, when a login command is requested through a specific ID according to a security level, the agent server 300 may perform an authentication procedure not only for the specific ID but also for another ID which is set to be authenticated in solidarity with the specific ID.

Specifically, for example, when information regarding a specific ID is received from one of the plurality of mobile terminals 100, the agent server 300 may set the specific ID to an ID of a first security level which can independently access a facility or information requiring an access authority, or an ID of a second security level which can access a facility or information requiring an access authority dependently according to a login state of the ID of the first security level even if validity of the login command regarding the ID is verified.

In addition, when information regarding a specific ID is received and a security level of the received ID is set, and then a login command regarding the ID is requested, the agent server 300 may determine whether the ID requesting the login command is the ID of the first security level or the ID of the second security level. When the ID requesting the login command is the ID of the first security level, the agent server 300 may verify only the validity of the login command regarding the ID of the first security level. However, when the ID requesting the login command is the ID of the second security level, the agent server 300 may verify the validity of the login command regarding the ID of the second security level only in the state where the ID of the first security level, which is set to authenticate in solidarity with the ID of the second security level, is logged in.

Specifically, for example, in the case of the first mobile terminal 100-1 performing the authentication procedure for the agent server 300 using the ID of the first security level and the second mobile terminal 100-2 performing the authentication procedure for the agent server 300 using the ID of the second security level, the first mobile terminal 100-1 can independently access the facility or information requiring the access authority when its own authentication procedure is determined to be valid, but the second mobile terminal 100-2 can access the facility or information requiring the access authority only when the mobile terminal 100-1 is logged in although its own authentication procedure is determined to be valid. That is, when the first mobile terminal 100-1 is logged out, the second mobile terminal 100-2 cannot access the facility or information requiring the access authority although its own authentication procedure is determined to be valid. Therefore, the agent server 300 may perform the solidarity authentication procedure among the plurality of users of a set user group, rather than the authentication procedure using a personal password or biometric information.

Through this, the variable biometric information-based complex authentication system of the present disclosure performs the solidarity authentication procedure that is applicable to a cloud service or a web storage service, such that security regarding information requiring an access authority can be enhanced.

The agent server 300 may provide one or more IDs of the second security level that are set to be able to access the facility or information requiring the access authority only in the state where the ID of the first security level is logged in.

In addition, the agent server 300 may variably change whether the ID intending to access the facility or information requiring the access authority is the ID of the first security level or the ID of the second security level with respect to the facility or information requiring the access authority according to settings.

In addition, when there are a plurality of facilities or a plurality of pieces of information requiring an access authority, the agent server 300 may individually set the ID intending to access the facility or information requiring the access authority to the ID of the first security level or the ID of the second security level with respect to respective facilities or information requiring the access authority.

Specifically, for example, when an ID "α" is set to the ID of the first security level and an ID "β" is set to the ID of the second security level with respect to specific information "A" as shown in FIG. 4, both ID "α" and ID "β" may be set to the ID of the second security level and an ID "γ" may be set to the ID of the first security level with respect to another specific information "B".

As described above, the agent server 300 may individually set each ID to the ID of the first security level or the ID of the second security level with respect to each of the facilities or pieces of information requiring the access authority, and such settings may be variably changed as described above.

To achieve this, the agent server 300 includes a communication unit 310, a controller 320, and a storage 330.

The communication unit 310 of the agent server may be connected with the mobile terminal 100 and the variable biometric information management server 200 by using a communication network, and may be provided to perform Internet communication.

Specifically, when a login command regarding a specific ID is requested from the mobile terminal 100, the communication unit 310 may receive variable biometric information from the mobile terminal 100 and the variable biometric information management server 200.

The controller 320 of the agent server is provided to control elements of the agent server 300 and to perform the overall tasks of the variable biometric information management server 200.

Specifically, when the login command regarding the specific ID is requested from the mobile terminal 100, the controller 320 may control to receive variable biometric information including a real value from the mobile terminal 100 via the communication unit 310, and may request, from the variable biometric information management server 200, variable biometric information which is stored along with the information regarding the specific ID, but does not include the real value and includes only information regarding a figure or a form of a graph indicating a variation in a specific section, and may receive the variable biometric information.

When the variable biometric information is received from the mobile terminal 100 and the variable biometric information management server 200, the controller 320 may extract the information regarding the figure or the form of the graph indicating the variation in the specific section from the variable biometric information received from the mobile terminal 100, and may compare the extracted information regarding the figure or the form of the graph indicating the variation in the specific section, and the variable biometric information received from the variable biometric information management server 200, and may verify validity of the login command regarding the specific ID.

In addition, when information regarding a specific ID is received from one of the plurality of mobile terminals 100, the controller 320 may set the specific ID to the ID of the first security level or the ID of the second security level, or may change a security level of a predetermined ID.

The storage 330 of the agent server may be provided to store programs and data necessary for performing the tasks of the agent server 300.

Additionally, the mobile terminal 100, which is an element of the complex authentication system of the present disclosure, may be substituted with a computer (PC) provided with a means for collecting variable biometric information, such as a smart scale, a smart blood pressure gauge, a smart blood glucose monitor, a smart watch, a smart band, and a smart shoe insole.

Furthermore, the above-mentioned biometric information is an example of biometric information which variably changes according to a user's emotion state, health state, time, temperature, or other external environments, rather than being information which is permanent with respect to a specific user, and biometric information that has not been mentioned above can be applied to the present disclosure if it variably changes.

Figure 5:
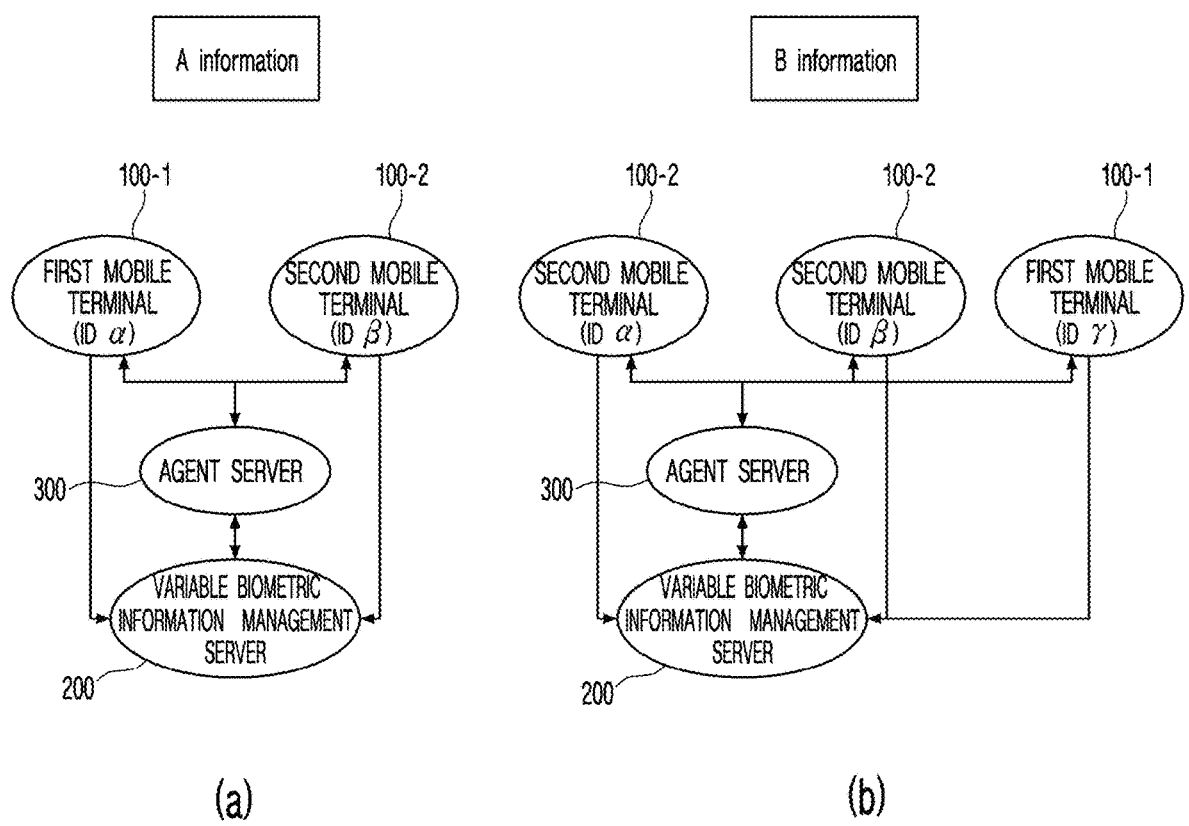
FIG. 5 is a flowchart provided to illustrate a variable biometric information-based complex authentication method according to an embodiment of the present disclosure.
Figure 6:
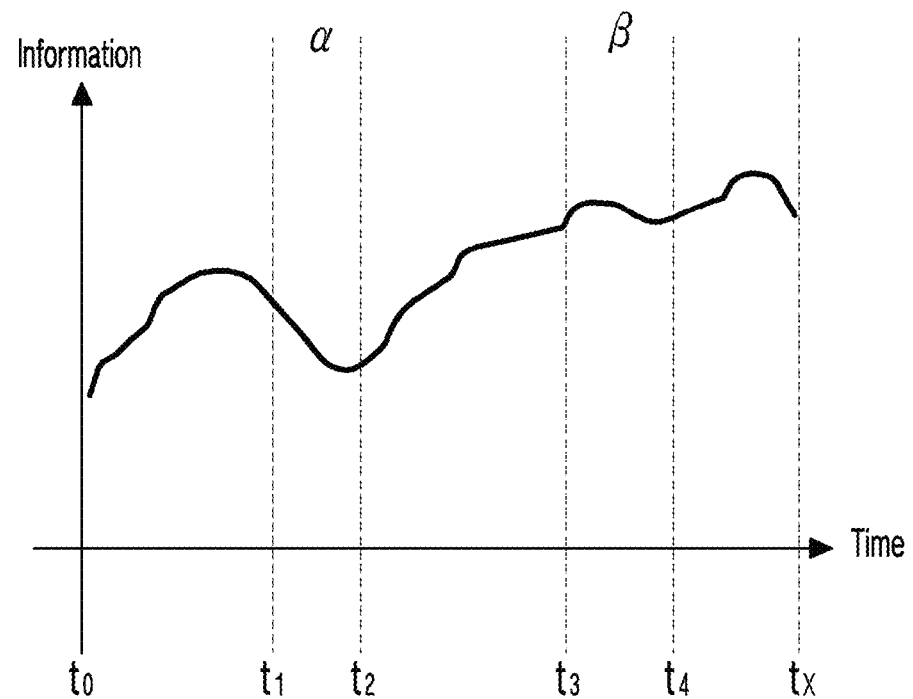
FIG. 6 is a view provided to illustrate variable biometric information which is collected and stored according to a variable biometric information-based complex authentication method according to an embodiment of the present disclosure.
Figure 7:
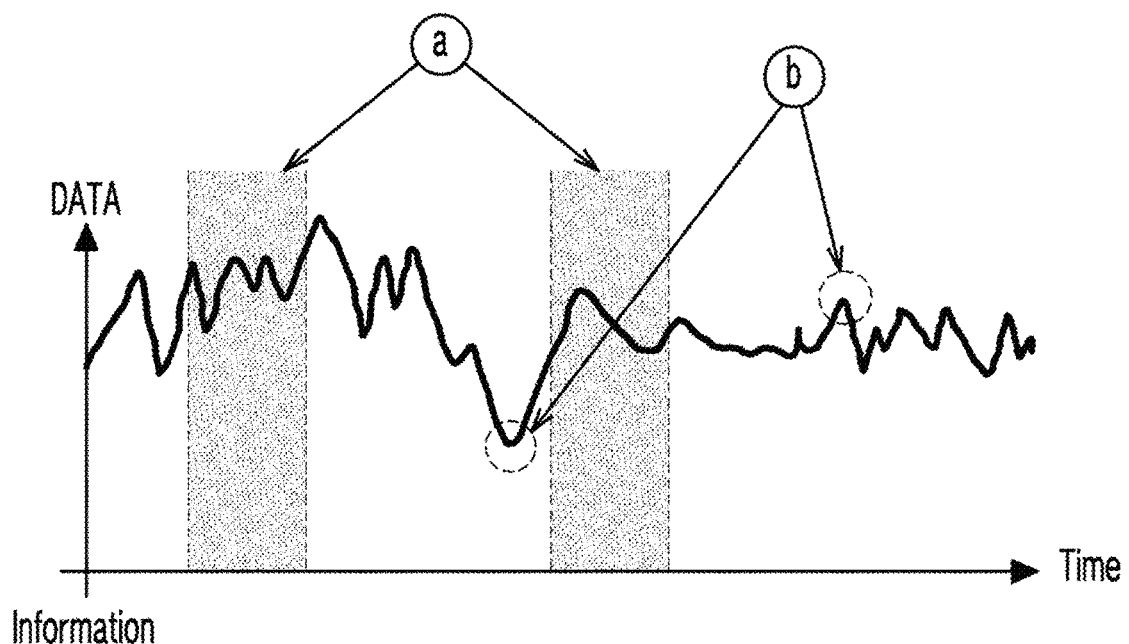
FIG. 7 is a view provided to illustrate variable biometric information which is collected and stored according to a variable biometric information-based complex authentication method according to an embodiment of the present disclosure.

FIG. 5 is a flowchart provided to illustrate a variable biometric information-based complex authentication method according to an embodiment of the present disclosure, and FIGS. 6 and 7 are views provided to illustrate variable biometric information which is collected and stored according to a variable biometric information-based complex authentication method according to an embodiment of the present disclosure. In addition, FIGS. 8 to 11 are views provided to illustrate a process of determining equivalence between variable biometric information according to a variable biometric information-based complex authentication method according to an embodiment of the present disclosure.

Hereinafter, a variable biometric information-based complex authentication method (hereinafter, referred to as a "complex authentication method") according to an embodiment will be described with reference to FIGS. 5 to 11.

The complex authentication method according to an embodiment is provided to perform an authentication procedure using personal variable biometric information, which changes according to times and environments, so as to inhibit a damage even if the biometric information used in the authentication procedure using the complex authentication system is leaked, and also, is provided to perform the authentication procedure by combining different types of variable biometric information or by combining variable biometric information collected from a plurality of users.

First, the mobile terminal 100 may generate information regarding an ID that intends to access a facility or information requiring an access authority (S305), and, when variable biometric information is collected (S310), the mobile terminal 100 may match the generated information regarding the ID and the variable biometric information each other, and store the matched information (S315). In addition, the mobile terminal 100 may transmit the stored variable biometric information to the variable biometric information management server 200 (S320).

In briefly describing the variable biometric information, the variable biometric information may have a value corresponding time. When data of predetermined information is collected, the data may be outputted in the form of a figure or a graph indicating a variation in a specific section as shown in FIG. 6.

For example, the mobile terminal 100 may collect variable biometric information that can be outputted in the form of a graph, and may store the collected variable biometric information in the unit of a predetermined time, and may add information regarding time to the variable biometric information and store the variable biometric information.

In this case, however, the form of the graph may be variously expressed according to a value of time and a value of information which are reflected on the graph.

Specifically, when a time interval reflected on the graph with respect to specific variable biometric information is set to hours or minutes, the same variable biometric information may be expressed by a graph of a gentle slope or a graph of a steep slope according to a set time interval. Accordingly, the variable biometric information may be diversely utilized according to an analysis method.

For example, with respect to variable biometric information to which a specific time, rather than seconds or minutes, should be applied like blood pressure, equivalence between information may be determined by comparing graph information which changes with time. With respect to such variable biometric information, outputting a graph showing a value of information of a specific time (for example, 8 o'clock a.m.) makes it easier to determine equivalence between information than outputting a graph showing data at time intervals of seconds or minutes like a body fat percentage or abdominal visceral fat.

In addition, such variable biometric information includes sensitive information related to user's personal information, diseases, or health state, and thus, when such information is leaked, there may be concern about a damage caused by an illegal use of a password, and also, a more serious damage may be caused by personal information leakage.

Accordingly, the mobile terminal 100 may collect variable biometric information, but may not transmit a real value of the collected variable biometric information to the variable biometric information management server 200, and may transmit only information regarding a figure or a form of a graph indicating a variation in a specific section, along with information regarding an ID. Therefore, even when the variable biometric information transmitted to the variable biometric information management server 200 is leaked, a damage resulting therefrom can be minimized or inhibited.

In addition, the variable biometric information management server 200 may accumulate and store the variable biometric information including only the information regarding the figure or the form of the graph according to the information regarding the ID. However, when the mobile terminal requests to discard variable biometric information stored for a specific ID, the variable biometric information management server 200 may discard the variable biometric information stored for the specific ID.

In addition, the variable biometric information management server 200 may accumulate and store variable biometric information, transmitted along with information regarding a specific ID after the stored variable biometric information is discarded, according to the information regarding the ID.

In addition, although the mobile terminal 100 transmits the real value of variable biometric information to the variable biometric information management server 200, the mobile terminal 100 may encrypt a real value of variable biometric information to which first time information ($\alpha$) is added, and a real value of variable biometric information to which second time information (β) is added, in order to inhibit a damage caused by the leakage of variable biometric information, and then may transmit the encrypted values. Therefore, when validity of a login command is verified, equivalence between the encrypted real values of the variable biometric information may be determined, and validity of a login command regarding a specific ID may be verified.

In particular, when the variable biometric information to which the first time information (α) is added and the variable biometric information to which the second time information (β) is added are encrypted, identification information corresponding to a specific ID matched with variable biometric information and time information may be utilized as a key value of a seed key for encryption. Therefore, equivalence between variable biometric information matched with the same identification information and added with the same time information may be determined even after the variable biometric information is encrypted. Therefore, a damage caused by the leakage of biometric information can be minimized and validity of a login command regarding a specific ID can be verified.

However, when the pieces of variable biometric information to which the same time information is added are compared with each other, the variable biometric information may be outputted in the form of a pattern (a) of information values during a specific time interval, or in the form of an information value (b) at a specific time, as shown in FIG. 6.

In this case, according to the pattern (a) of the information values during the specific time interval, equivalence between the variable biometric information may be determined based on a graph outputting a specific change value according to the contraction and expanding of the heart during the specific time interval, like an electrocardiogram (ECG) graph.

In addition, the method for outputting the variable biometric information in the form of a figure or a graph indicating a variation in a specific section may be diversely applied. A width of a section and setting information of the section, which influence the form of the graph, may be diversely set by considering user's setting, type of biometric information, a collection period and a collection time, physiological characteristics of biometric information. Since collected data is also recorded with numerical values, the data may be expressed by graphs of various forms by adjusting specific values of the information and the time. Accordingly, even with respect to biometric information having a small variation, it is possible to make a visual form of data like a specific figure or a form or pattern of a graph.

For example, even when a body fat percentage minimally changes from 19% to 19.2%, morphological changes may appear in a graph according to whether data is expressed by the graph in the unit of 10% or 1%. Therefore, the data can be utilized as a figure, a form of a graph, or pattern data for being utilized in personal identification and authentication.

For example, referring to FIG. 7, the mobile terminal 100 may set times from t0 to tx to a time unit, and may collect and store variable biometric information corresponding to values corresponding to times t0 to tx, and may add information regarding time to the variable biometric information and store the information.

However, as the information regarding the time, information regarding times t1 to t2 and information regarding times t3 to t4 may be individually generated. Therefore, even if variable biometric information is stored in one time unit, information regarding a specific time may be identified and may assist in enhancing accuracy of the authentication procedure.

The accuracy of the authentication procedure will be described in more detail with description of a procedure of verifying validity of a login command.

Meanwhile, when information regarding a specific ID is received from one of the plurality of mobile terminals 100, the agent server 300 may set the specific ID to an ID of a first security level which can independently access a facility or information requiring an access authority, or an ID of a second security level which can access a facility or information requiring an access authority dependently according to a login state of the ID of the first security level even if validity of the login command regarding the ID is verified (S325).

When a login command regarding an ID is requested, the agent server 300 may determine whether the ID requesting the login command is the ID of the first security level or the ID of the second security level. When the ID requesting the login command is the ID of the first security level, the agent server 300 may verify only the validity of the login command regarding the ID of the first security level.

Specifically, when the ID requesting the login command is the ID of the first security level (S325-Y), and the mobile terminal 100 requests a login command regarding the specific ID to the agent server 300 (S330-Y), the agent server 300 may receive respective pieces of variable biometric information from the mobile terminal 100 and the agent server 300 (S335)

In this case, the agent server 300 may receive variable biometric information including a real value from the mobile terminal 100 and may extract information regarding a figure or a form of a graph indicating a variation in a specific section, and may receive, from the variable biometric information management server 200, variable biometric information that does not include a real value and includes only information regarding a figure or a form of a graph indicating a variation in a specific section. The agent server 300 may compare the extracted information regarding the figure or the form of the graph indicating the variation in the specific section and the received information regarding the figure or the form of the graph indicating the variation in the specific section, and may verify the validity of the login command (S340).

In addition, when it is determined that the extracted information regarding the figure or the form of the graph indicating the variation in the specific section and the received information regarding the figure or the form of the graph indicating the variation in the specific section are equal to each other (S340-Y), the agent server 300 may determine that the login command regarding the specific ID is valid (S345).

On the other hand, when the ID requesting the login command is the ID of the second security level (S325-N) and the mobile terminal 100 requests a login command regarding the specific ID to the agent server 300 (S350-Y), the agent server 300 may verify the validity of the login command regarding the ID of the second security level only in the state where the ID of the first security level, which is set to authenticate in solidarity with the ID of the second security level, is logged in (S355).

For example, when it is determined that the ID of the first security level, which is set to authenticate in solidarity with the specific ID set to the second security level, is logged in (S355-Y), the agent server 300 may receive respective pieces of variable biometric information from the mobile terminal 100 and the agent server 300 (S335).

That is, the second mobile terminal 100-2 using the specific ID set to the second security level can access the facility or information requiring the access authority only when the first mobile terminal 100-1 is logged in (S355-Y) although its own authentication procedure is determined to be valid, and cannot access the facility or information requiring the access authority when the first mobile terminal 100-1 is logged out (S355-N) although its own authentication procedure is valid.

Meanwhile, when verifying the validity of the login command by comparing the extracted information regarding the figure or the form of the graph indicating the variation in the specific section and the received information regarding the figure or the form of the graph indicating the variation in the specific section, the agent server 300 may compare time information added to the variable biometric information received from the mobile terminal 100 and time information added to the variable biometric information received from the variable biometric information management server 200, and may determine equivalence therebetween, and, when it is determined that the respective pieces of time information are equal to each other, the agent server 300 may determine equivalence between the respective pieces of variable biometric information, and may verify the validity of the login command regarding the specific ID.

Figure 8:
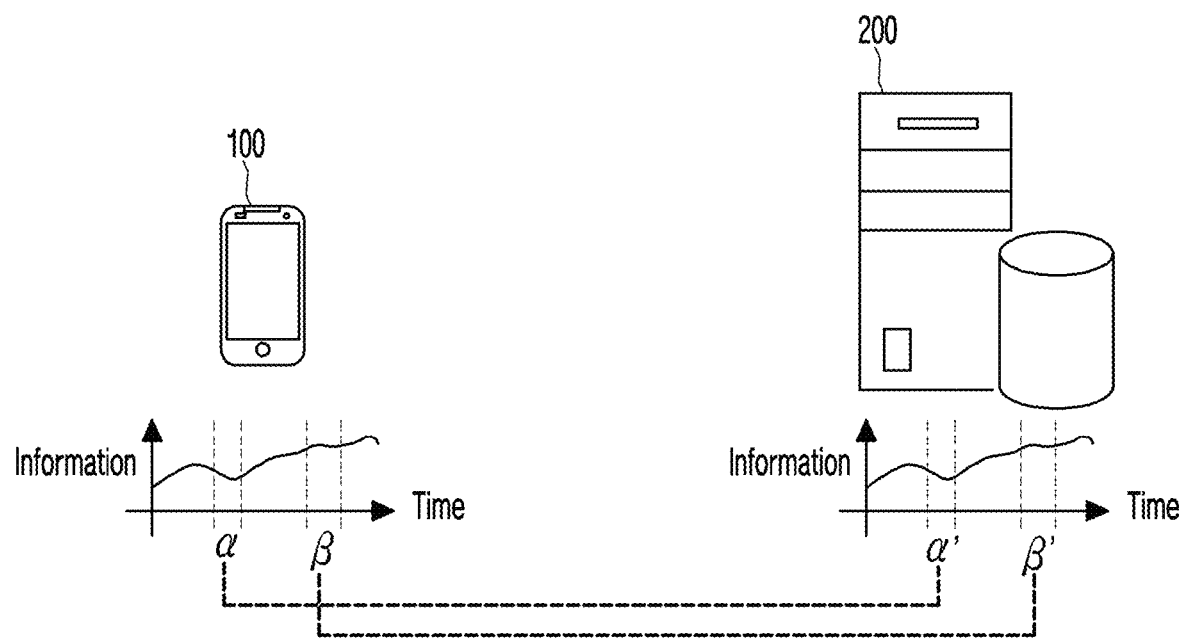
FIG. 8 is a view provided to illustrate a process of determining equivalence between variable biometric information according to a variable biometric information-based complex authentication method according to an embodiment of the present disclosure.

For example, as shown in FIG. 8, the agent server 300 may compare time information ($\alpha$) added to the variable biometric information received from the mobile terminal 100, and respective pieces of time information ($\alpha'$ and $\beta'$) added to the variable biometric information received from the variable biometric information management server 200, and may determine equivalence therebetween. When it is determined that there exists the same time information ($\alpha'$), the agent server 300 may compare the pieces of variable biometric information to which the same time information ($\alpha'$) is added, and may determine equivalence therebetween.

Figure 9:
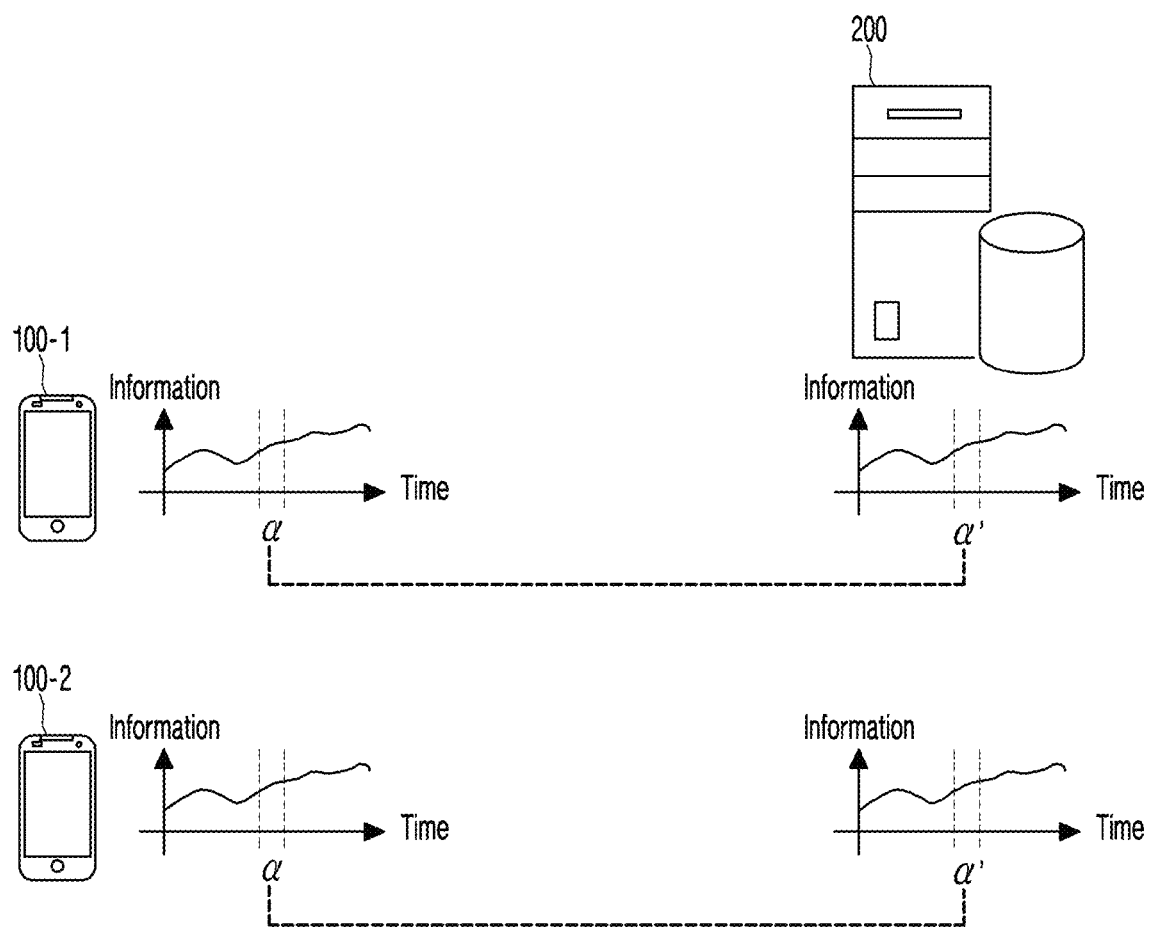
FIG. 9 is a view provided to illustrate a process of determining equivalence between variable biometric information according to a variable biometric information-based complex authentication method according to an embodiment of the present disclosure.

Meanwhile, when there are a plurality of accessed mobile terminals 100 as shown in FIG. 9, the agent server 300 may differentially set the mobile terminals 100 to the first mobile terminal 100-1 requesting a login command using the ID of the first security level, and the second mobile terminal 100-2 requesting a login command using the ID of the second security level.

In this case, in the case of the first mobile terminal 100-1, validity of the login command may be independently verified, and, in the case of the second mobile terminal 100-2, validity of the login command may be dependently verified only in the state where the first mobile terminal 100-1 set to authenticate in solidarity with another terminal is logged in. Therefore, the security of the authentication procedure can be enhanced.

Figure 10:
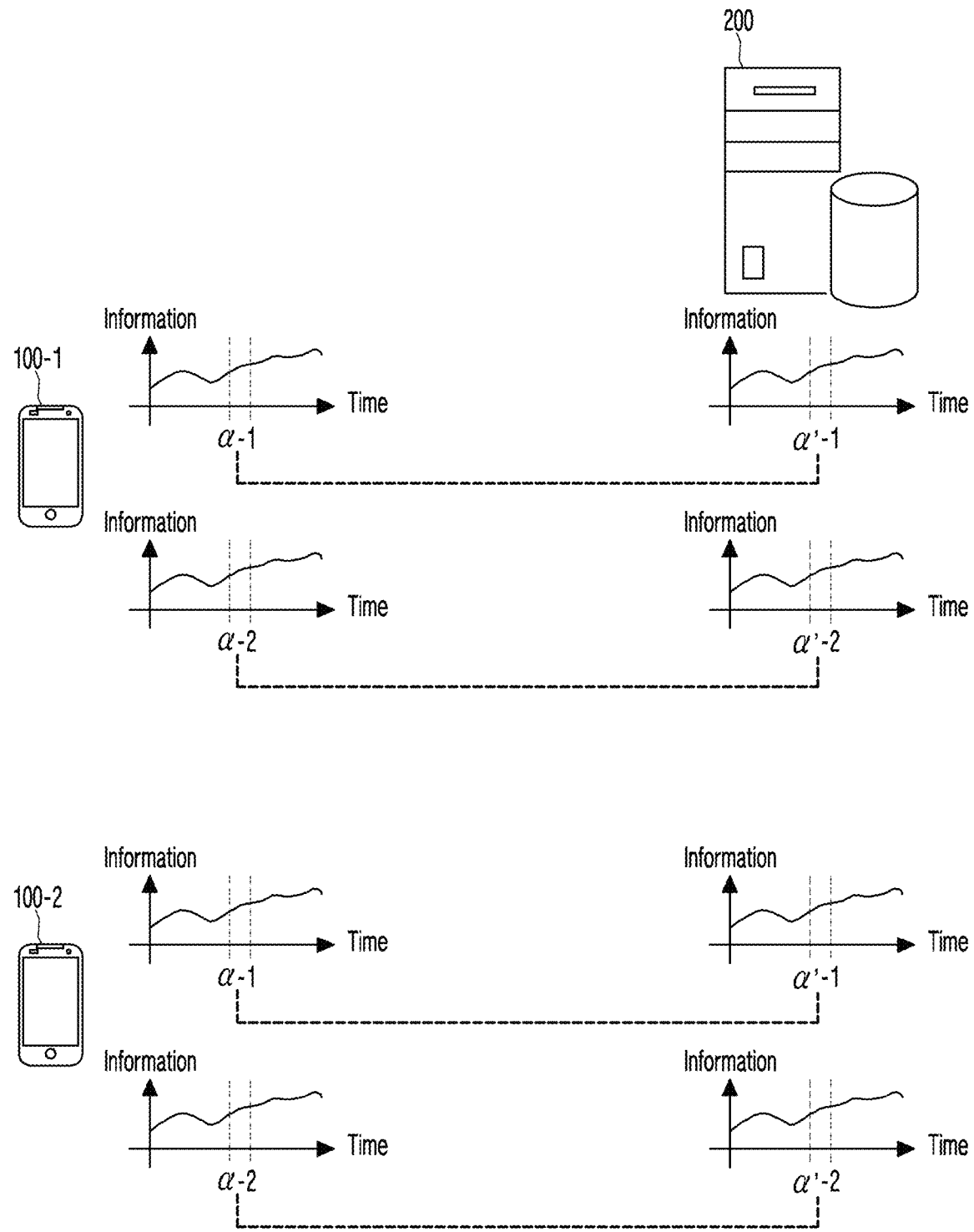
FIG. 10 is a view provided to illustrate a process of determining equivalence between variable biometric information according to a variable biometric information-based complex authentication method according to an embodiment of the present disclosure.

Meanwhile, when two or more types of variable biometric information are collected by the mobile terminal 100 as shown in FIG. 10, the mobile terminal 100 may match respective pieces of classification information to the respective pieces of variable biometric information along with identification information corresponding to the ID, such that the respective pieces of variable biometric information can be identified.

In addition, when the mobile terminals 100 are differentially set to the first mobile terminal 100-1 using the ID of the first security level and the second mobile terminal 100-2 using the ID of the second security level, and a login command regarding a specific ID is requested by the first mobile terminal 100-1, the agent server 300 may receive, from the mobile terminal 100 and the variable biometric information management server 200, respective pieces of variable biometric information stored along with the information regarding the ID requesting the login command, and may identify the received pieces of variable biometric information according to classification information and may individually determine equivalence therebetween.

For example, the agent server 300 may identify the received pieces of variable biometric information as first variable biometric information and second variable biometric information according to classification information. The agent server 300 may compare first variable biometric information received from the mobile terminal 100 and first variable biometric information received from the variable biometric information management server 200, and determine equivalence therebetween. Likewise, the agent server 300 may compare second variable biometric information received from the mobile terminal 100 and second variable biometric information received from the variable biometric information management server 200, and determine equivalence therebetween.

In this case, as pieces of variable biometric information having different time information are complexly compared in the above-described example, pieces of variable biometric information having different classification information may be respectively compared to determine equivalence therebetween, and also, they may be compared by diversely setting an average of the first variable biometric information and the second variable biometric information or a complex arithmetic relation between two pieces of variable biometric information.

For example, when average weight data of a user A and weight data of both feet of the user A are collected, the average weight data may be referred to as first variable biometric information, and the weight data of both feet of the user A may be referred to as second variable biometric information. In this case, the agent server 300 may determine whether average weight data received from the mobile terminal 100 and average weight data received from the variable biometric information management server 200 are equal to each other, and may determine whether weight data of both feet received from the mobile terminal 100 and weight data of both feet received from the variable biometric information management server 200 are equal to each other. When it is determined that all pieces of variable biometric information are equal to each other, the agent server 300 may determine that the validity of the login command is verified.

In another example, the agent server 300 may calculate a value which is right foot's weight data of the weight data of both feet subtracted from the average weight data, and may compare a subtraction value of the variable biometric information received from the mobile terminal 100 and a subtraction value of the variable biometric information received from the variable biometric information management server 200, and may determine equivalence therebetween.

In this case, the both feet's weight data may be collected by using a biometric information collecting means such as a smart shoe insole.

In addition, when the mobile terminals 100 are differentially set to the first mobile terminal 100-1 using the ID of the first security level and the second mobile terminal 100-2 using the ID of the second security level, and a login command regarding a specific ID is requested by the second mobile terminal 100-2, the agent server 300 may determine whether the first mobile terminal 100-1, set to authenticate in solidarity with the second mobile terminal 100-2, is logged in by using the ID of the first security level. Only when it is determined that the first mobile terminal 100-1 is logged in by using the ID of the first security level, the agent server 300 may receive, from the mobile terminal 100 and the variable biometric information management server 200, respective pieces of variable biometric information stored along with the information regarding the ID requesting the login command, and may identify the received pieces of variable biometric information according to classification information and may individually determine equivalence therebetween.

Herein, as described above, the agent server 300 according to an embodiment is limited to the login command for convenience of explanation, but, when an access authority regarding information stored in a network server is obtained or an authentication procedure is required like an electronic payment command, validity of a corresponding command may be verified in the same method, and the command may be performed.

Figure 11:
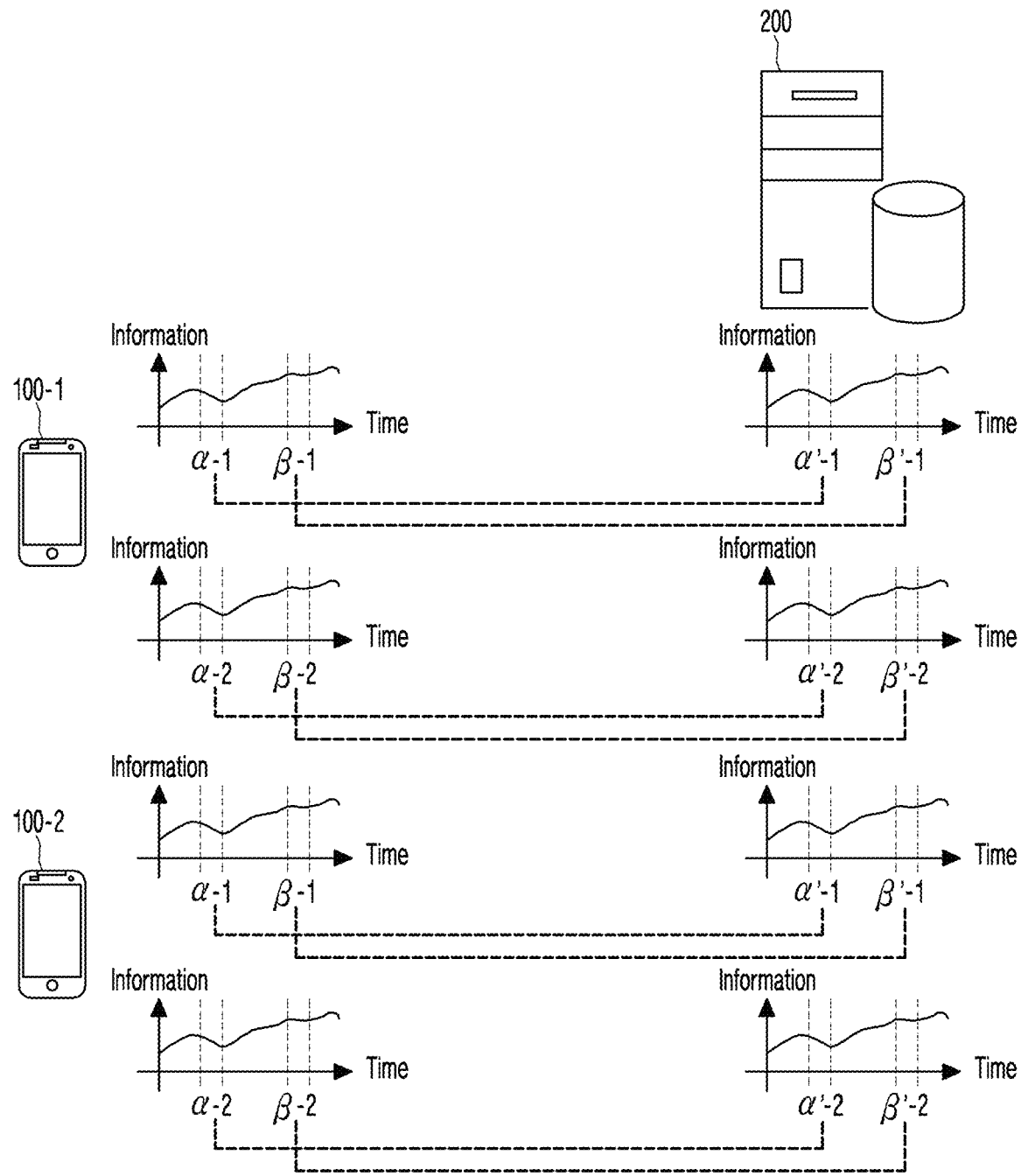
FIG. 11 is a view provided to illustrate a process of determining equivalence between variable biometric information according to a variable biometric information-based complex authentication method according to an embodiment of the present disclosure.

In addition, in another example, when there are a plurality of accessed mobile terminals 100 and a plurality of types of variable biometric information are collected by the plurality of mobile terminals 100 as shown in FIG. 11, the agent server 300 may determine equivalence between pieces of variable biometric information to which one same time information is added, and also, may individually determine equivalence with respect to two or more pieces of time information, and may complexly process the results of determining equivalence.

Specifically, the agent server 300 may compare variable biometric information to which first time information ($\alpha$) is added, and variable biometric information to which the same time information ($\alpha'$) as the first time information ($\alpha$) is added, and may determine equivalence therebetween, and may compare variable biometric information to which second time information ($\beta$) is added, and variable biometric information to which the same time information ($\beta'$) as the second time information ($\beta$) is added, and may determine equivalence therebetween. In this case, only when all of the results of determining equivalence indicate equivalence, the validity of the login command regarding the specific ID may be recognized.

In addition to the respective results of determining equivalence, the agent server 300 may diversely set an average of the variable biometric information to which the first time information ($\alpha$) is added, and of the variable biometric information to which the second time information ($\beta$) is added, or a complex arithmetic relation between two pieces of variable biometric information, and may compare the two pieces of variable biometric information.

For example, a sum value, a subtraction value, a multiplication value, or an average value regarding data of average weight 70.5 kg of October in 2016 and data of average weight of 71.5 kg of December in 2016 may be calculated, and equivalence between variable biometric information may be determined although direct numerical values of the variable biometric information are not compared.

In addition, the mobile terminal 100 may match time information and classification information to collected variable biometric information, and store the matched information. When pieces of variable biometric information to which different time information is added are collected by the plurality of mobile terminals 100, the agent server 300 may identify the respective pieces of variable biometric information according to the time information.

Specifically, when the mobile terminals 100 are differentially set to the first mobile terminal 100-1 using the ID of the first security level and the second mobile terminal 100-2 using the ID of the second security level, and a login command regarding a specific ID is requested by the first mobile terminal 100-1, the agent server 300 may receive, from the mobile terminal 100 and the variable biometric information management server 200, respective pieces of variable biometric information stored along with the information regarding the ID requesting the login command, and may identify the received pieces of variable biometric information according to classification information and time information, and may individually determine equivalence therebetween. To this end, the validity of the login command regarding the ID used to request the login command is verified.

On the other hand, when the mobile terminals 100 are differentially set to the first mobile terminal 100-1 using the ID of the first security level and the second mobile terminal 100-2 using the ID of the second security level, and a login command regarding a specific ID is requested by the second mobile terminal 100-1, the agent server 300 may determine whether the first mobile terminal 100-1, set to authenticate in solidarity with the second mobile terminal 100-2, is logged in by using the ID of the first security level. Only when it is determined that the first mobile terminal 100-1 is logged in by using the ID of the first security level, the agent server 300 may receive, from the mobile terminal 100 and the variable biometric information management server 200, respective pieces of variable biometric information stored along with the information regarding the ID requesting the login command, and may identify the received pieces of variable biometric information according to classification information and time information, and may individually determine equivalence therebetween.

Accordingly, the security of the authentication procedure can be enhanced by combining different types of variable biometric information from among variable biometric information, such as user's weight, body fat percentage, blood pressure, temperature, breathing rate, heart rate, blood glucose, muscle mass, total body water, protein, abdominal visceral fat, skeletal muscle mass, basal metabolic rate, exercise, number of steps, sleeping pattern, weight load pattern of both feet, and paces, or combining variable biometric information of a plurality of users.

While embodiments of the present disclosure have been described with reference to the accompanying drawings, specific embodiments for effectively describing the technical idea of the present disclosure are particularly shown and described. Therefore, it will be understood by those of ordinary skill in the art that the present disclosure is not limited to the above-described exemplary embodiments, and various changes in form and details may be made therein without departing from the spirit and scope of the present disclosure as defined by the following claims. In addition, the scope of the present disclosure should be defined not by the embodiments described above but by the appended claims. In addition, the meaning and the scope of the claims and all changes or changed forms derived from equivalents thereto should be interpreted as being included in the scope of the present disclosure.

The invention claimed is:

1. A variable biometric information-based complex authentication system comprising:
   a plurality of mobile terminals configured to generate first information regarding an ID that intends to access a facility or second information requiring an access authority, and to collect variable biometric information, such that the first information regarding the ID and the variable biometric information are stored all together;
a variable biometric information management server configured to receive the first information regarding the ID and the variable biometric information from the plurality of mobile terminals, and to store the first information regarding the ID and the variable biometric information; and
an agent server configured to, when a mobile terminal requests a login command regarding the ID, compare variable biometric information received from the variable biometric information management server and variable biometric information received from the plurality of mobile terminals, and to verify validity of the login command regarding the ID,
wherein the agent server is configured to, when first information regarding a specific ID is received from one of the plurality of mobile terminals, set the specific ID to an ID of a first security level which is able to independently access the facility or the second information requiring the access authority, or an ID of a second security level which is able to access the facility or the second information requiring the access authority dependently according to a login state of the ID of the first security level even when validity of the login command regarding the ID is verified,
wherein the agent server is configured to provide one or more IDs of the second security level that are set to be able to access the facility or the second information requiring the access authority only in a state where the ID of the first security level is logged in,
wherein the agent server is configured to, when a login command regarding the ID is requested, determine whether the ID requesting the login command is the ID of the first security level or the ID of the second security level, and
wherein the agent server is configured to, when the ID requesting the login command is the ID of the first security level, verify only validity of the login command regarding the ID of the first security level, and, when the ID requesting the login command is the ID of the second security level, verify validity of the login command regarding the ID of the second security level only in the state where the ID of the first security level, which is set to authenticate in solidarity with the ID of the second security level, is logged in.

2. The variable biometric information-based complex authentication system of claim 1, wherein the agent server is configured to variably change whether the ID intending to access the facility or information requiring the access authority is the ID of the first security level or the ID of the second security level with respect to the facility or information requiring the access authority according to settings.

3. The variable biometric information-based complex authentication system of claim 1, wherein the agent server is configured to, when there are a plurality of facilities or a plurality of pieces of information requiring the access authority, individually set the ID, intending to access the facility or information requiring the access authority, to the ID of the first security level or the ID of the second security level with respect to the respective facilities or the respective piece of information requiring the access authority.

4. The variable biometric information-based complex authentication system of claim 1, wherein the variable biometric information comprises one or more pieces of information from among user's weight, body fat percentage, blood pressure, temperature, breathing rate, heart rate, blood glucose, muscle mass, total body water, protein, abdominal visceral fat, skeletal muscle mass, basal metabolic rate, exercise, number of steps, sleeping pattern, weight load pattern of both feet, and paces.

5. A variable biometric information-based complex authentication system comprising:
a plurality of mobile terminals configured to generate first information regarding an ID that intends to access a facility or second information requiring an access authority, and to collect variable biometric information, such that the first information regarding the ID and the variable biometric information are stored all together;
a variable biometric information management server configured to receive the first information regarding the ID and the variable biometric information from the plurality of mobile terminals, and to store the first information regarding the ID and the variable biometric information; and
an agent server configured to, when a mobile terminal requests a login command regarding the ID, compare variable biometric information received from the variable biometric information management server and variable biometric information received from the plurality of mobile terminals, and to verify validity of the login command regarding the ID,
wherein the agent server is configured to, when first information regarding a specific ID is received from one of the plurality of mobile terminals, set the specific ID to an ID of a first security level which is able to independently access the facility or the second information requiring the access authority, or an ID of a second security level which is able to access the facility or the second information requiring the access authority dependently according to a login state of the ID of the first security level even when validity of the login command regarding the ID is verified, and
wherein the plurality of terminals are configured to collect the variable biometric information and to avoid transmitting a real value of the collected variable biometric information to the variable biometric information management server, and is configured to transmit only information regarding a figure or a form of a graph indicating a variation in a specific section.

6. The variable biometric information-based complex authentication system of claim 5, wherein the agent server is configured to, when a login command regarding the specific ID is requested, compare a figure or a form of a graph included in variable biometric information received from the mobile terminal, and a figure or a form of a graph included in variable biometric information received from the variable biometric information management server on a real time basis, and to verify validity of the login command.

7. The variable biometric information-based complex authentication system of claim 6, wherein the variable biometric information management server is configured to accumulate and store the variable biometric information including only information regarding the figure or the form of the graph according to the information regarding the ID, and, when the mobile terminal requests to discard variable biometric information stored for the specific ID, to discard the variable biometric information stored for the specific ID, and to accumulate and store variable biometric information, transmitted along with the information regarding the specific ID after the stored variable biometric information is discarded, according to the information regarding the ID.

8. The variable biometric information-based complex authentication system of claim 5, wherein the mobile terminal is configured to, when two or more types of variable biometric information are collected, match respective pieces of classification information to the collected pieces of variable biometric information along with the information regarding the ID, such that the respective types of variable biometric information are identified.

9. The variable biometric information-based complex authentication system of claim 8, wherein the agent server is configured to, when the two or more types of variable biometric information are collected, individually determine equivalence between first variable biometric information and second variable biometric information to which different classification is matched, and to verify validity of login commands regarding respective IDs generated by the plurality of mobile terminals.

* * * * *